(12) United States Patent
Goertzen et al.

(10) Patent No.: US 8,062,003 B2
(45) Date of Patent: Nov. 22, 2011

(54) SYSTEM AND METHOD FOR PROVIDING OXYGEN

(75) Inventors: Gerold Goertzen, Brunswick, OH (US); William A. Null, Jr., Sullivan, OH (US)

(73) Assignee: Invacare Corporation, Elyria, OH (US)

( * ) Notice: Subject to any disclaimer, the term of this patent is extended or adjusted under 35 U.S.C. 154(b) by 314 days.

(21) Appl. No.: 11/231,603

(22) Filed: Sep. 21, 2005

(65) Prior Publication Data

US 2007/0065301 A1    Mar. 22, 2007

(51) Int. Cl.
F04B 1/12    (2006.01)
F04B 27/08    (2006.01)

(52) U.S. Cl. .......................... 417/269; 417/529

(58) Field of Classification Search ............ 417/203.25, 417/204, 205, 206.21, 207.16, 272, 273, 417/464, 245–268, 244, 560, 568, 555.1, 417/496, 522, 527, 528, 529; 137/512, 625.37–625.39, 606, 512.2, 454.4; 92/79; 384/57; 128/204.18
See application file for complete search history.

(56) References Cited

U.S. PATENT DOCUMENTS

| | | | |
|---|---|---|---|
| 519,423 A | 4/1903 | Harral et al. | |
| 875,297 A | 12/1907 | Stanley | |
| 1,764,655 A * | 6/1930 | Spreen | 137/533.19 |
| 1,873,878 A * | 8/1932 | Goldsborough | 417/265 |
| 1,936,167 A * | 11/1933 | Kniskern | 55/344 |
| 1,964,679 A * | 6/1934 | Springfield | 417/238 |
| 2,057,158 A | 10/1936 | Moffitt | |
| 2,141,057 A | 12/1938 | Whiles | |
| 2,151,825 A * | 3/1939 | Aikman | 384/428 |
| 2,550,369 A | 4/1951 | Moreillon | |
| 2,628,015 A * | 2/1953 | Neugebauer et al. | 417/203 |
| 2,944,627 A | 7/1960 | Skarstrom | |
| 3,119,410 A * | 1/1964 | Noecker | 137/512 |
| 3,149,778 A * | 9/1964 | Enemark | 417/415 |
| 3,203,357 A * | 8/1965 | Delorme | 417/454 |
| 3,216,648 A * | 11/1965 | Ford | 417/53 |
| 3,313,091 A | 4/1967 | Berlin | |
| 3,448,664 A | 6/1969 | Hulsing | |
| 3,510,233 A * | 5/1970 | Habegger et al. | 417/454 |
| 3,839,946 A | 10/1974 | Paget | |
| 3,898,047 A | 8/1975 | Cramer | |
| 3,924,968 A | 12/1975 | Gaines et al. | |
| 3,964,866 A | 6/1976 | Shelby | |
| 4,013,429 A | 3/1977 | Sircar et al. | |

(Continued)

FOREIGN PATENT DOCUMENTS

CA    2228779    8/1998

(Continued)

OTHER PUBLICATIONS

PCT/US2006/036398 Written Opinion dated May 5, 2007, International filing date Sep. 19, 2006.

(Continued)

*Primary Examiner* — Devon C Kramer
*Assistant Examiner* — Amene Bayou
(74) *Attorney, Agent, or Firm* — Calfee, Halter & Griswold LLP (57) ABSTRACT

A home care oxygen system includes an inline compressor that has all the check valves and gas flow passages between cylinders located in the cylinder head. Only a single check valve is used for each cylinder. The crankshaft is built up from a shaft with eccentrics and spacers.

22 Claims, 9 Drawing Sheets

U.S. PATENT DOCUMENTS

| Number | Kind | Date | Name | Ref |
|---|---|---|---|---|
| 4,194,890 | A | 3/1980 | McCombs et al. | |
| 4,222,750 | A | 9/1980 | Gauthier et al. | |
| 4,253,524 | A * | 3/1981 | Erickson | 166/325 |
| 4,263,018 | A | 4/1981 | McCombs et al. | |
| 4,331,455 | A | 5/1982 | Sato | |
| 4,334,833 | A | 6/1982 | Gozzi | |
| 4,349,357 | A | 9/1982 | Russell | |
| 4,353,682 | A | 10/1982 | Linnert et al. | |
| 4,428,372 | A | 1/1984 | Beysel et al. | |
| 4,449,990 | A | 5/1984 | Tedford, Jr. | |
| 4,456,440 | A * | 6/1984 | Korner | 417/540 |
| 4,465,436 | A | 8/1984 | Schonwald | |
| 4,505,333 | A * | 3/1985 | Ricks, Sr. | 166/267 |
| 4,516,424 | A | 5/1985 | Rowland | |
| 4,552,571 | A | 11/1985 | Dechene | |
| 4,573,886 | A * | 3/1986 | Maasberg et al. | 417/454 |
| 4,576,616 | A | 3/1986 | Mottram et al. | |
| 4,610,700 | A | 9/1986 | Miller et al. | |
| 4,627,860 | A | 12/1986 | Rowland | |
| 4,636,226 | A | 1/1987 | Canfora | |
| 4,638,694 | A * | 1/1987 | Slee | 82/18 |
| 4,643,651 | A * | 2/1987 | Couillard | 417/265 |
| 4,645,428 | A | 2/1987 | Arregui et al. | |
| 4,670,223 | A | 6/1987 | Delachapelle | |
| 4,673,415 | A | 6/1987 | Stanford | |
| 4,698,075 | A | 10/1987 | Dechene | |
| 4,706,664 | A | 11/1987 | Snook et al. | |
| 4,765,804 | A | 8/1988 | Lloyd-Williams et al. | |
| 4,844,059 | A | 7/1989 | Koch | |
| 4,860,803 | A | 8/1989 | Wells | |
| 4,867,766 | A | 9/1989 | Campbell et al. | |
| 4,869,733 | A | 9/1989 | Stanford | |
| 4,880,443 | A | 11/1989 | Miller et al. | |
| 4,905,685 | A | 3/1990 | Olsson et al. | |
| 4,922,900 | A | 5/1990 | Kiske et al. | |
| 4,948,391 | A | 8/1990 | Noguchi | |
| 4,957,107 | A | 9/1990 | Sipin | |
| 4,974,554 | A | 12/1990 | Emery | |
| 4,979,882 | A | 12/1990 | Wipf | |
| 4,983,190 | A | 1/1991 | Varrando et al. | |
| 4,991,616 | A | 2/1991 | Fabregat | |
| 5,020,974 | A * | 6/1991 | Searle | 417/246 |
| 5,033,940 | A | 7/1991 | Baumann | |
| 5,049,039 | A | 9/1991 | Knoth et al. | |
| 5,071,453 | A | 12/1991 | Hradek et al. | |
| 5,078,580 | A * | 1/1992 | Miller et al. | 417/265 |
| 5,078,757 | A | 1/1992 | Rottner et al. | |
| 5,144,945 | A | 9/1992 | Nishino et al. | |
| 5,154,737 | A | 10/1992 | Jenkins et al. | |
| 5,163,978 | A | 11/1992 | Leavitt et al. | |
| 5,195,874 | A | 3/1993 | Odagiri | |
| 5,199,423 | A | 4/1993 | Harral et al. | |
| 5,207,806 | A | 5/1993 | Lagree et al. | |
| 5,237,987 | A | 8/1993 | Anderson et al. | |
| 5,248,320 | A | 9/1993 | Garrett et al. | |
| 5,326,231 | A | 7/1994 | Pandeya et al. | |
| 5,354,361 | A | 10/1994 | Coffield | |
| 5,405,249 | A | 4/1995 | Benson | |
| 5,474,595 | A | 12/1995 | McCombs | |
| 5,490,871 | A | 2/1996 | Coates et al. | |
| 5,531,807 | A | 7/1996 | McCombs | |
| 5,584,669 | A | 12/1996 | Becker | |
| 5,593,291 | A | 1/1997 | Lynn | |
| 5,593,478 | A | 1/1997 | Hill et al. | |
| 5,704,964 | A | 1/1998 | Kaneko et al. | |
| 5,730,778 | A | 3/1998 | Hill et al. | |
| 5,755,561 | A * | 5/1998 | Couillard et al. | 417/246 |
| 5,823,186 | A | 10/1998 | Rossen et al. | |
| 5,858,062 | A | 1/1999 | McCulloh et al. | |
| 5,863,186 | A * | 1/1999 | Green et al. | 417/53 |
| 5,875,783 | A | 3/1999 | Kullik | |
| 5,893,275 | A | 4/1999 | Henry | |
| 5,893,944 | A | 4/1999 | Dong | |
| 5,897,305 | A * | 4/1999 | Roddis | 417/566 |
| 5,988,165 | A | 11/1999 | Richey, II et al. | |
| 6,132,177 | A | 10/2000 | Loprete et al. | |
| 6,183,211 | B1 * | 2/2001 | Wood | 417/254 |
| 6,302,107 | B1 | 10/2001 | Richey, II et al. | |
| 6,352,057 | B1 | 3/2002 | Drecq | |
| 6,393,802 | B1 | 5/2002 | Bowser et al. | |
| 6,422,237 | B1 | 7/2002 | Engel et al. | |
| 6,478,857 | B2 | 11/2002 | Czabala | |
| 6,508,638 | B2 * | 1/2003 | Sagar | 417/569 |
| 6,651,658 | B1 | 11/2003 | Hill et al. | |
| 6,684,755 | B2 | 2/2004 | Boyd et al. | |
| 6,805,122 | B2 | 10/2004 | Richey, II et al. | |
| 6,823,891 | B2 * | 11/2004 | Schulze et al. | 137/512 |
| 6,889,726 | B2 * | 5/2005 | Richey et al. | 141/83 |
| 6,923,180 | B2 | 8/2005 | Richey, II et al. | |
| 7,178,552 | B2 * | 2/2007 | Takeda | 137/512 |
| 7,204,249 | B1 | 4/2007 | Richey, II et al. | |
| 7,244,107 | B2 * | 7/2007 | Cheng | 417/266 |
| 7,294,170 | B2 | 11/2007 | Richey, II et al. | |
| 7,296,591 | B2 * | 11/2007 | Moe et al. | 137/454.4 |
| 2002/0014237 | A1 | 2/2002 | Richey, II | |
| 2004/0103895 | A1 * | 6/2004 | Richey et al. | 128/203.25 |
| 2006/0000474 | A1 | 1/2006 | Richey et al. | |
| 2008/0118373 | A1 | 5/2008 | Richey, II | |

FOREIGN PATENT DOCUMENTS

| | | |
|---|---|---|
| DE | 1 403 963 A1 | 11/1968 |
| EP | 64177 | 11/1984 |
| EP | 239713 | 10/1987 |
| EP | 860647 | 8/1998 |
| EP | 1334741 A1 | 8/2003 |
| GB | 374540 | 6/1932 |
| GB | 581 476 A | 10/1946 |
| JP | 63-307101 | 12/1988 |
| JP | 64-028208 | 1/1989 |
| JP | 11 257222 A | 9/1999 |
| WO | 83/03983 | 12/1983 |
| WO | 87/01599 | 3/1987 |
| WO | 99/16529 | 4/1999 |
| WO | 02/34368 | 5/2002 |
| WO | 03/024569 | 3/2003 |
| WO | 2007/038065 | 4/2007 |

OTHER PUBLICATIONS

PCT/US2006/036398 Search Report, International filing date Sep. 19, 2006.

International Search Report from PCT/US02/29164 dated Dec. 13, 2002.

International Search Report and Written Opinion from PCT/US01/45433 dated Apr. 18, 2002.

International Preliminary Examination Report from PCT/US01/45433 dated Sep. 11, 2002.

International Search Report from PCT/US98/19282 dated May 10, 1999.

Request for Ex Parte Reexamination Transmittal Form (2 pgs.), Request for Reexamination (26 pgs.) and Certificate of Mailing (2 pgs.), Information Disclosure Statement (2 pgs) submitted to U.S. Patent Office on Aug. 16, 2006 for reexamination of U.S. Patent No. 5,988,165 Control No. 90/008167.

Office action from U.S. Appl. No. 08/942,063, mailed Oct. 30, 1998.

Amendment from U.S. Appl. No. 08/942,063 dated May 13, 1999.

Supplemental Amendment from U.S. Appl. No. 08/942,063 dated Feb. 23, 1999.

Notice of Allowance from U.S. Appl. No. 08/942,063, mailed Jul. 14, 1999.

Office action from U.S. Appl. No. 09/154,442, mailed Sep. 8, 2000.

Amendment from U.S. Appl. No. 09/154,442 dated Dec. 7, 2000.

Interview Summary from U.S. Appl. No. 09/154,442, mailed Jan. 24, 2001.

Notice of Allowance from U.S. Appl. No. 09/154,442, mailed Apr. 25, 2001.

Notice of Allowance from U.S. Appl. No. 09/154,442, mailed Jul. 17, 2001.

Office action from U.S. Appl. No. 09/952,763, mailed Jan. 29, 2003.

Amendment from U.S. Appl. No. 09/952,763 dated Apr. 24, 2003.

Notice of Allowance from U.S. Appl. No. 09/952,763, mailed Jul. 8, 2003.

Office action from U.S. Appl. No. 10/605,754, mailed May 17, 2004.

Response from U.S. Appl. No. 10/605,754 dated Oct. 20, 2004.

Office action from U.S. Appl. No. 10/605,754, mailed Nov. 15, 2004.
Interview Summary from U.S. Appl. No. 10/605,754 dated Feb. 2, 2005.
Response from U.S. Appl. No. 10/605,754 dated Mar. 14, 2005.
Notice of Allowance from U.S. Appl. No. 10/605,754, mailed Apr. 5, 2005.
Office action from U.S. Appl. No. 09/695,612, mailed May 7, 2003.
Response from U.S. Appl. No. 09/695,612 dated Nov. 7, 2003.
Office action from U.S. Appl. No. 09/695,612, mailed Feb. 6, 2004.
Response from U.S. Appl. No. 09/695,612 dated Jul. 9, 2004.
Office action from U.S. Appl. No. 09/695,612, mailed Sep. 30, 2004.
Response from U.S. Appl. No. 09/695,612 dated Feb. 2, 2005.
Office action from U.S. Appl. No. 09/695,612, mailed Mar. 22, 2005.
Response from U.S. Appl. No. 09/695,612 dated Sep. 14, 2005.
Office action from U.S. Appl. No. 09/695,612, mailed Oct. 19, 2005.
Response from U.S. Appl. No. 09/965,612 dated Dec. 8, 2005.
Office action from U.S. Appl. No. 09/695,612, mailed Jan. 25, 2006.
Response from U.S. Appl. No. 09/695,612 dated Mar. 6, 2006.
Office action from U.S. Appl. No. 09/695,612, mailed Mar. 29, 2006.
Response from U.S. Appl. No. 09/695,612 dated Jun 5, 2006.
Notice of Allowance from U.S. Appl. No. 09/695,612, mailed Jun. 26, 2006.
Office action from U.S. Appl. No. 11/180,395, mailed Jun. 19, 2006.
Response from U.S. Appl. No. 11/180,395 dated Sep. 21, 2006.
Supplemental Response from U.S. Appl. No. 11/180,395 dated Oct. 18, 2006.
Office action from U.S. Appl. No. 11/180,395, mailed Dec. 1, 2006.
Response from U.S. Appl. No. 11/180,395 dated Jun. 1, 2007.
Notice of Allowance from U.S. Appl. No. 11/180,395, mailed Jun. 19, 2007.
Supplemental Notice of Allowability from U.S. Appl. No. 11/180,395, mailed Aug. 17, 2007.
Office action from Control No. 90/008,167, mailed Dec. 12, 2007.
Response from Control 90/008,167 dated Feb. 12, 2008.
Final Office action from Control No. 90/008,167 dated Mar. 17, 2008.
Response from Control No. 90/008,167 dated May 14, 2008.
Office action from Canadian application No. 2,426,685 date Mar. 9, 2010.
RIX Industries, "RIX SA Air Compressors—Oil-Free Breathing Air to 4,500 PSIG", 2 pgs, undated.
International Search Report and Written Opinion from PCT/US10/45705 dated Oct. 5, 2010.

* cited by examiner

SYSTEM AND METHOD FOR PROVIDING OXYGEN

BACKGROUND

Oxygen has many important medical uses including, for example, assisting patients that have congestive heart failure or other diseases. Supplemental oxygen allows patients to receive more oxygen than is present in the ambient atmosphere. Systems and methods for delivering such oxygen typically include a compressor as a component. U.S. Pat. No. 5,988,165, for example, discloses the use of an inline compressor for this purpose. US Published Application No. 2004/0103895, for example, discloses the use of a radial compressor for this purpose.

SUMMARY OF THE INVENTION

In one aspect the invention relates to a compressor for compressing a gas, including a cylinder assembly having a plurality of cylinders of varying displacements arranged adjacent each other inline. A plurality of pistons are received in the cylinders. A drive mechanism is connected with the pistons. A cylinder head is connected with the cylinder assembly, the cylinder head including a gas inlet for the compressor and a gas outlet for the compressor. The compressor includes a plurality of gas flow passages that extend between and interconnect the plurality of cylinders, all of the gas flow passages being located in the cylinder head.

In another aspect the invention relates to a compressor for compressing a gas, including a cylinder assembly having a plurality of cylinders of varying displacements arranged adjacent each other including a largest displacement cylinder and a smallest displacement cylinder, and a plurality of pistons received in the cylinders. A drive mechanism is connected with the pistons for driving the pistons. A cylinder head assembly connected with the cylinder assembly includes a gas inlet and a gas outlet and a single gas flow path therebetween. An inlet check valve is in the gas flow path between the gas inlet and the largest cylinder. A single check valve is in the gas flow path between each two adjacent cylinders. An outlet check valve in the gas flow path between the smallest cylinder and the gas outlet. (In other embodiments more than one check valve could be provided in the gas flow path between two adjacent cylinders.)

In another aspect the invention relates to a compressor for compressing a gas, including a cylinder assembly having a plurality of cylinders of varying displacements arranged adjacent each other. A plurality of pistons are received in the cylinders, and a drive mechanism is connected with the pistons for driving the pistons. The drive mechanism includes a crankshaft, the crankshaft comprising a plurality of eccentric bodies mounted on a single shaft.

In another aspect the invention relates to an apparatus for providing oxygen-enriched gas for use by a patient, including an oxygen source for providing oxygen-enriched gas, the oxygen source having a first output and a second output. A compressor is connected in fluid communication with the first output of the oxygen source for compressing oxygen-enriched gas provided by the oxygen source, the compressor being adapted to be connected with a portable tank to enable filling of the portable tank with compressed oxygen-enriched gas from the compressor. A patient device is for providing oxygen-enriched gas to a patient, the patient device being connected with the second output of the oxygen source. The compressor comprises a cylinder head connected with the cylinder assembly, the cylinder head including a gas inlet for the compressor and a gas outlet for the compressor, the cylinder head also including a plurality of gas flow passages that extend between and interconnect the cylinders, all of the gas flow passages being located in the cylinder head.

In another aspect the invention relates to a method of filling a portable tank with compressed oxygen-enriched gas, the method comprising the steps of:

directing oxygen-enriched gas from an oxygen source through a first output and a second output;

directing the first output of the oxygen source to a compressor;

compressing the oxygen-enriched gas in the compressor;

filling a portable tank with compressed oxygen-enriched gas from the compressor; and directing the second output of the oxygen source to a patient device for providing oxygen-enriched gas to a patient;

wherein the compressor comprises a cylinder head connected with the cylinder assembly, the cylinder head including a gas inlet for the compressor and a gas outlet for the compressor, the cylinder head also including a plurality of gas flow passages that extend between and interconnect the cylinders, all of the gas flow passages being located in the cylinder head.

BRIEF DESCRIPTION OF THE DRAWING

Further features and advantages of the present invention will become apparent to those of ordinary skill in the art to which the invention pertains from a reading of the following description together with the accompanying drawings, in which.

DETAILED DESCRIPTION OF PREFERRED EMBODIMENTS

Figure 1:
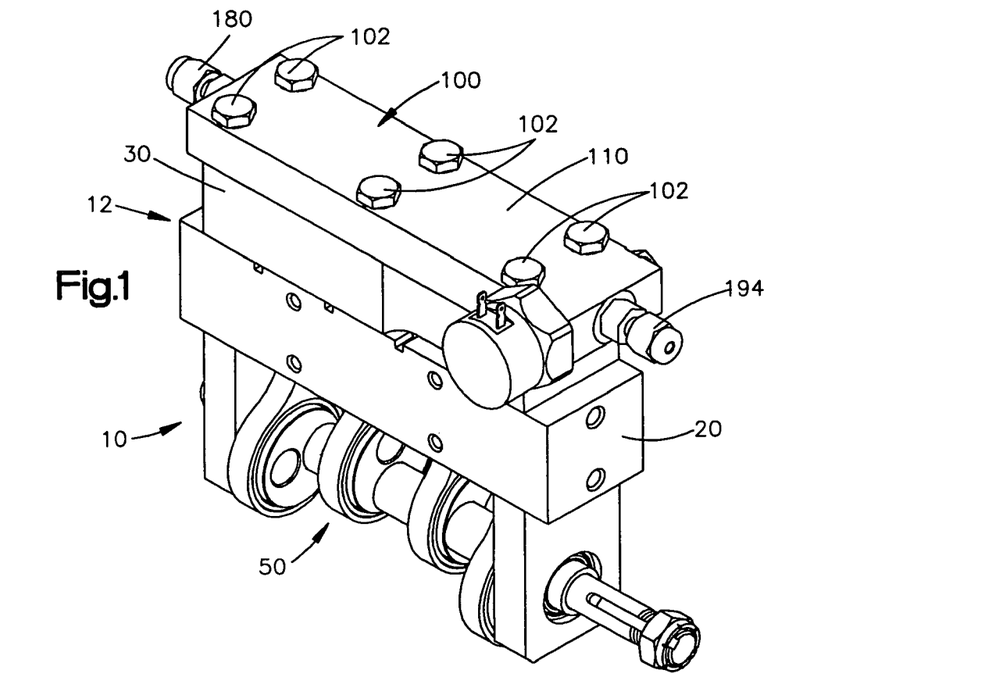
FIG. 1 is a perspective view of a compressor in accordance with a first embodiment of the invention.

FIG. 1 illustrates a compressor 10 that is one embodiment of the invention. The compressor 10 includes a cylinder assembly 12. The cylinder assembly preferably includes a lower cylinder block 20 and an upper cylinder block 30. The cylinder assembly in other embodiments could be a one-piece unit.

Figure 3:
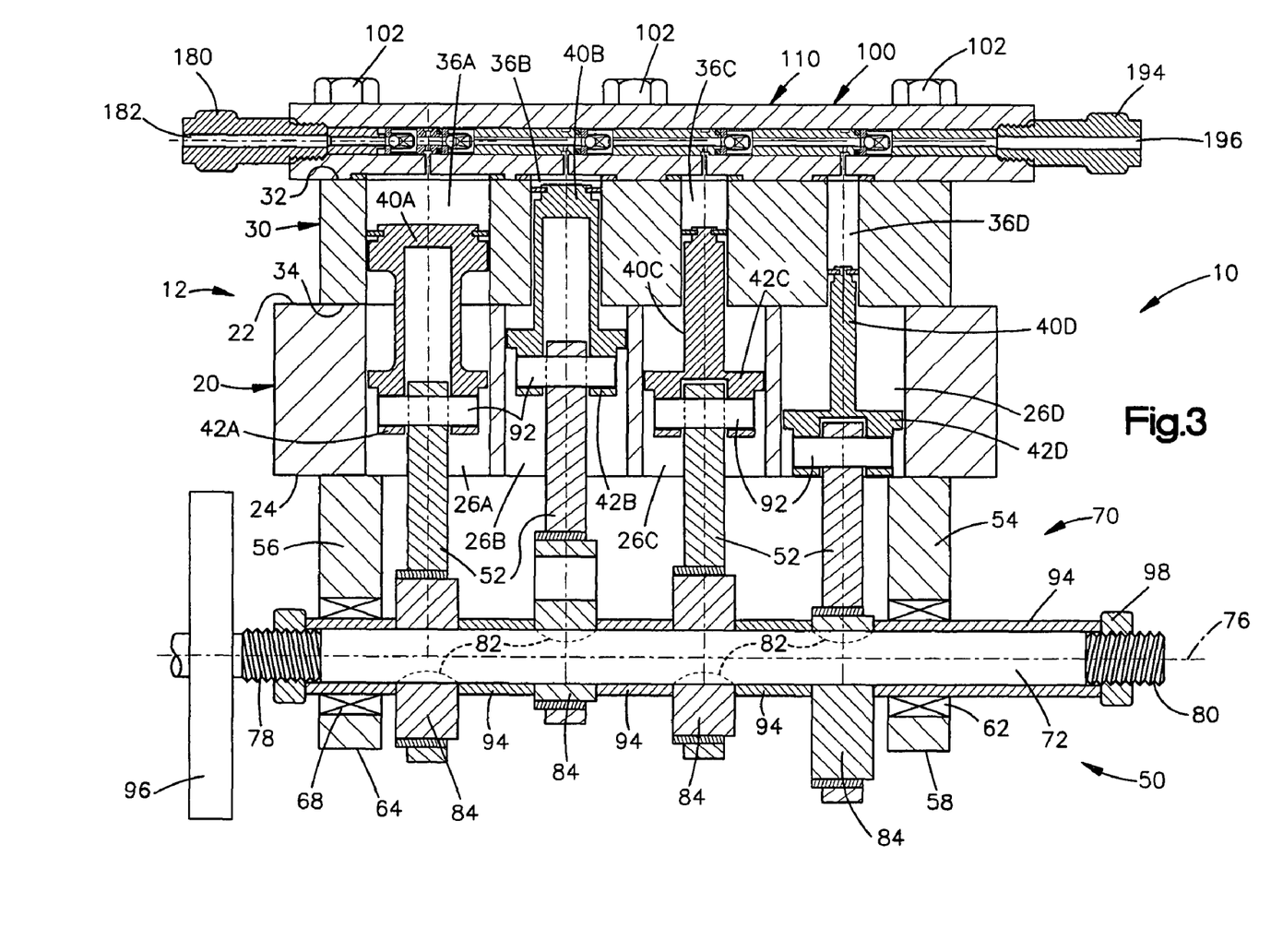
FIG. 3 is a sectional view of the compressor of FIG. 1.

Referring now to FIG. 3, the lower cylinder block 20 is formed in one embodiment as one piece (a monoblock) having parallel upper and lower end surfaces 22 and 24. The lower cylinder block 20 has four equal sized guide openings 26A-26D that extend between the upper and lower end surfaces 22 and 24. The guide openings 26A-26D are adjacent each other and are spaced apart along the length of the lower cylinder block 20. In the illustrated embodiment, the guide openings 26A-26D are spaced apart at equal intervals along the length of the lower cylinder block 20. In other embodiments, this spacing may change.

Figure 2:
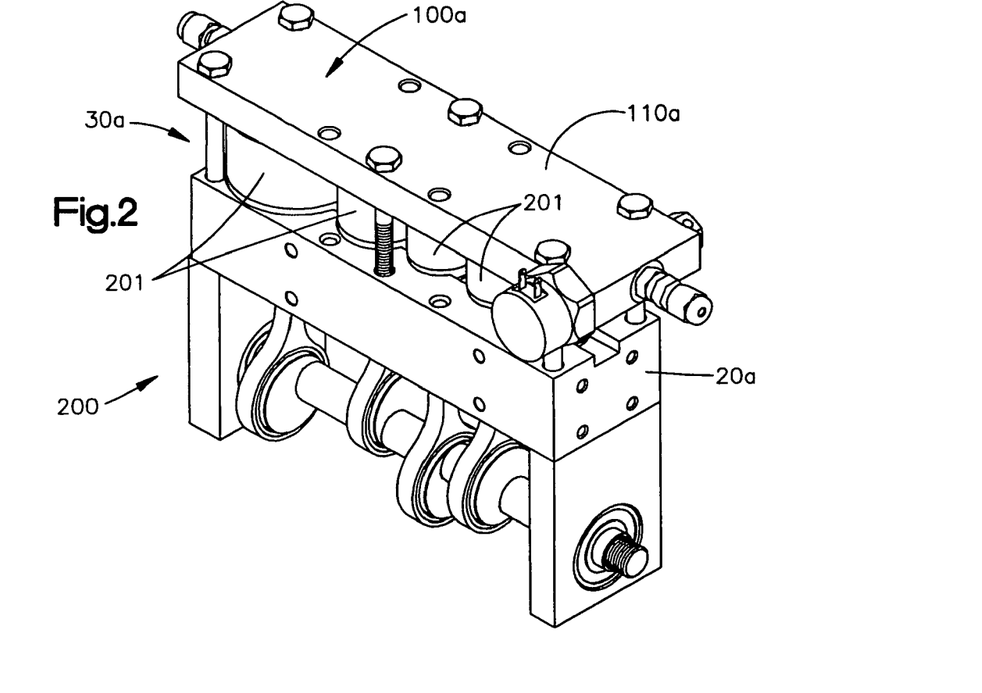
FIG. 2 is a perspective view of a compressor in accordance with a second embodiment of the invention.

In the illustrated embodiment, the upper cylinder block 30 is formed as one piece having parallel upper and lower end surfaces 32 and 34. In other embodiments, as described below with reference to the compressor 200 of FIGS. 2 and 10, for example, the upper cylinder block 30 could be formed as a plurality of separate cylinder sleeves. Whether the upper cylinder block is formed as a monoblock or as a plurality of separate cylinder sleeves is not dependent on the number of cylinders.

The upper cylinder block 30 has four openings 36A-36D that extend between the upper and lower end surfaces 32 and 34. The openings 36A-36D are spaced apart at equal intervals along the length of the upper cylinder block 30. In other embodiments, this spacing may be changed. The openings 36A-36D form the four cylinders of the compressor 10.

The cylinders 36A-36D are of varying diameters and as a result varying displacements. The invention is also applicable to cylinders having varying strokes and thereby varying displacements. The first cylinder 36A is the largest in diameter, the second cylinder 36B is smaller, the third cylinder is smaller yet, and the fourth cylinder is the smallest. The invention is applicable to compressors having more than four cylinders or fewer than four cylinders.

The lower end surface 34 of the upper cylinder block 30 is in abutting engagement with the upper end surface 22 of the lower cylinder block 20. The guide openings 26A-26D in the lower cylinder block align with the cylinders 36A-36D in the upper cylinder block 30.

The compressor includes a plurality of pistons 40A-40D that are associated in a one to one relationship with the cylinders 36A-36D. A first piston 40A is located in the first cylinder 36A and is supported for sliding (reciprocating) movement in the first cylinder. A second piston 40B is located in the second cylinder 36B and is supported for sliding (reciprocating) movement in the second cylinder. A third piston 40C is located in the third cylinder 36C and is supported for sliding (reciprocating) movement in the third cylinder. A fourth piston 40D is located in the fourth cylinder 36D and is supported for sliding (reciprocating) movement in the fourth cylinder.

The compressor 10 includes a plurality of guides 42A-D that are associated in a one to one relationship with the guide openings 26 and with the pistons 40A-40D. The guides 42A-D are driven by a crankshaft 50 and connecting rods 52, as described below. A first guide 42A is located in the first guide opening 26A and is supported for sliding (reciprocating) movement in the first guide opening. The first piston 40A is fixed for movement with the first guide 42A. The first piston 40A could be formed as one piece with the first guide 42A. Alternatively, the first piston 40A could be formed separately from then connected to the first guide 42A.

A second guide 42B is located in the first guide opening 26B and is supported for sliding (reciprocating) movement in the first guide opening. The second piston 40B is fixed for movement with the second guide 42B and could be formed as one piece with or separately from the second guide 42B. The second guide 42B is the same diameter as the first guide 42A, although the second piston 40B is smaller in diameter than the first piston 40A.

A third guide 42C is located in the third guide opening 26C and is supported for sliding (reciprocating) movement in the third guide opening. The third piston 40C is fixed for movement with the third guide 42C and could be formed as one piece with or separately from the third guide. The third guide 42C is the same diameter as the first guide 42A, although the third piston 40C is smaller in diameter than the second piston 40B.

A fourth guide 42D is located in the fourth guide opening 26D and is supported for sliding (reciprocating) movement in the fourth guide opening. The fourth piston 40D is fixed for movement with the fourth guide 42D and could be formed as one piece with or separately from the fourth guide. The fourth guide 42D is the same diameter as the first guide 42A, although the fourth piston 40D is smaller in diameter than the third piston 40C. This could be otherwise, in other embodiments.

The crankshaft 50 (described below in detail) is supported on first and second bearing supports 54 and 56 that are located one at either end of the compressor 10. In the illustrated embodiment, the first bearing support 54 has a generally rectangular configuration with a lower end portion 58 on which is supported a first bearing 62. Similarly, the second bearing support 56 has a generally rectangular configuration with a lower end portion 64 on which is supported a second bearing 68. There is an open space between the first and second bearing supports 54 and 56.

The crankshaft 50 forms part of a drive mechanism 70 of the compressor 10 for driving the pistons 40A-40D for reciprocating movement in the cylinders 36A-36D. The drive mechanism 70 as illustrated includes the guides 42; in other embodiments the crankshaft could be connected to the pistons more directly or in other manners, for example with connecting rods but not guides.

The crankshaft 50 in the illustrated embodiment is a multiple piece assembly, although it could be replaced with a one piece assembly. The crankshaft 50 includes a main shaft 72 having a generally cylindrical configuration defined by a cylindrical outer surface centered on a crank axis 76 of the compressor 10. The main shaft 72 has externally threaded opposite end portions 78 and 80. The main shaft 72 is received and supported in the first and second bearings 62 and 68.

A plurality of keyways 82 are formed in the outer surface 74 of the main shaft 72. The keyways 82 are spaced apart along the main shaft 72 at locations that correspond to the centers of the guide openings 26 in the cylinder assembly 12.

Figure 7:
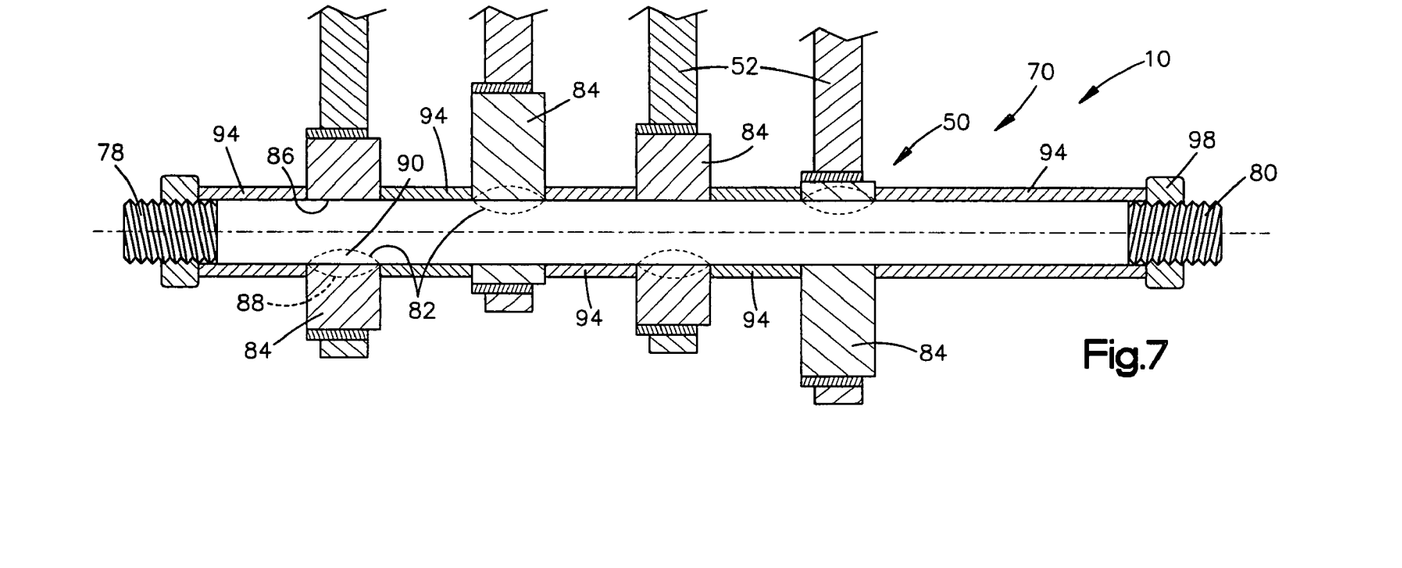
FIG. 7 is a view similar to FIG. 6 showing the crankshaft in an assembled condition.
Figure 9:
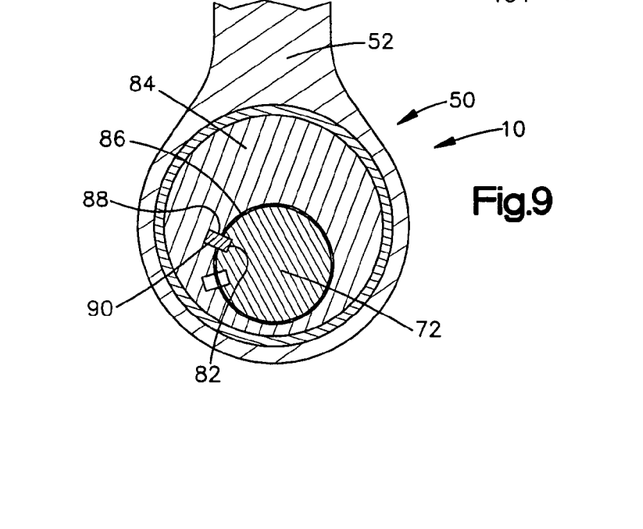
FIG. 9 is an enlarged sectional view of a portion of the crankshaft of FIG. 7.

As shown in FIGS. 7 and 9, the crankshaft 50 also includes a plurality of eccentric bodies 84. In the illustrated embodiment, the eccentric bodies 84 are all identical to each other, for ease of manufacturing and assembly. Each one of the eccentric bodies 84 has a circular configuration with a circular opening 86 that is not centered. Two keyways 88 are formed on the periphery of the opening 86.

For each eccentric body 84, a key 90 is located in the keyway 82 in the main shaft 72 and in the corresponding keyway 88 in the eccentric. The key 90 fixes the eccentric body 84 for rotation with the main shaft 72 about the crank axis 76. The provisions of the two keyways 88 in each eccentric body 84 allows the eccentric bodies to be fixed to the main shaft at two different positions about the axis, to set the timing of the pistons 40A-40D. Flipping the eccentric bodies by 180° would provide two additional positions, for a total of four positions.

As shown also in FIG. 3, a connecting rod 52 and a wrist pin 92 are connected between each eccentric body 84 and its associated guide 42. The connecting rods 52 extend through the open space between the bearing supports 54 and 56. Rotation of the main shaft 72 about the crank axis 76 results in reciprocating movement of the guides 42 in the guide openings 26 and thus of the pistons 40 in the cylinders 36.

The crankshaft 50 also includes a plurality of spacers 94. The spacers 94 are sleeves that are fitted on the main shaft, between adjacent eccentric bodies 84, to set the locations of the eccentric bodies on the main shaft. Other spacers 94 are located axially outward of the eccentric bodies 84 and radially inward of the first and second bearings 62 and 68. The spacers 94, which are closely fitted on the main shaft 72, effectively increase the diameter of the main shaft at the locations between the eccentric bodies 84, because all the elements of the crankshaft including the spacers are tightly clamped (axially) between the opposite ends of the crankshaft.

Figure 6:
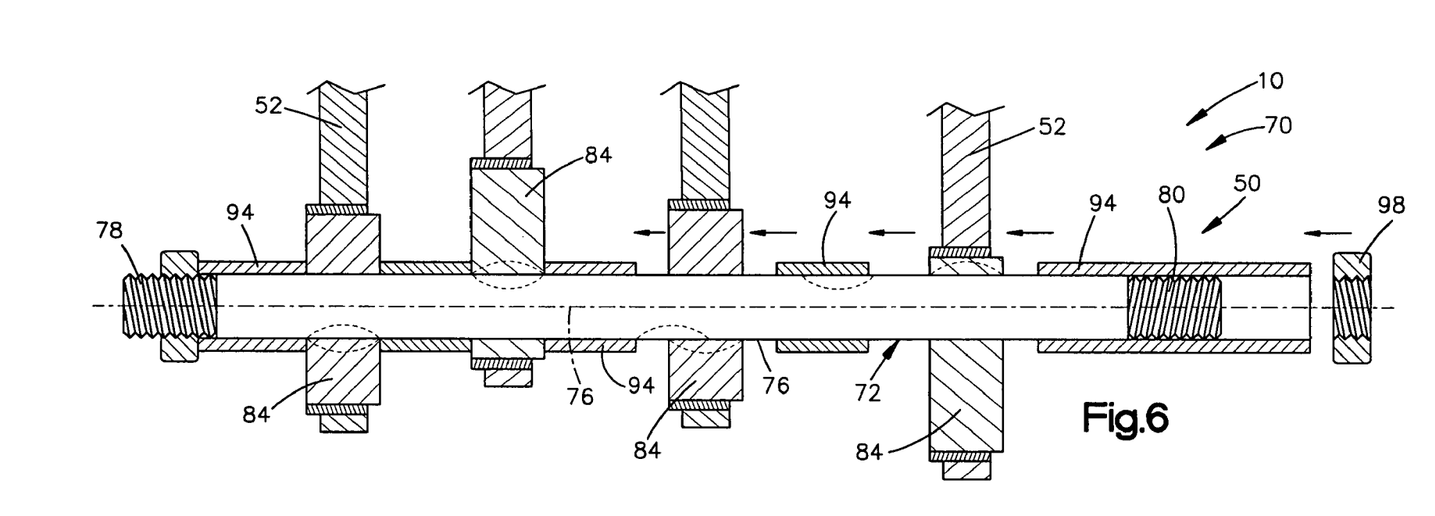
FIG. 6 is an enlarged sectional view of a crankshaft that forms part of the compressor of FIG. 1, shown in a condition being assembled.

The crankshaft 50 may be assembled in a manner as shown in FIGS. 6 and 7. The spacers 94 and the eccentric bodies 84 are slid longitudinally onto the main shaft 84 one at a time. The lengths of the individual spacers 94 are selected so that the eccentric bodies 84 are positioned correctly relative to the main shaft 72 and to the guide openings 26 in the lower cylinder block 20. A drive pulley 96 is located on one end portion 78 of the main shaft 72 and is held in position with a lock nut (see FIG. 3). On the other end of the crankshaft 50, a nut 98 is screwed on the other end portion 80 of the main shaft 75. The nut 98 when tightened down clamps the spacers 94 and the eccentric bodies 84 axially between the nut and the drive pulley 96 to form one rigid assembly.

As shown also in FIG. 3, the compressor 10 includes a cylinder head assembly 100. The cylinder head assembly 100 includes a cylinder head 110 that is fastened to the cylinder assembly 12 and to the other parts of the compressor with a plurality of fasteners. Specifically, the compressor 10 includes two bolts 102 at each end and two intermediate bolts 102. The bolts 102 extend through holes in the cylinder head 110, the upper cylinder block 30, and the lower cylinder block 20, and are threaded into bores in the bearing supports 54 and 56. When the bolts 102 are tightened down, the cylinder head 110, the cylinder assembly 12, and the bearing blocks 54 and 56 are clamped together into one rigid unit.

Figure 4:
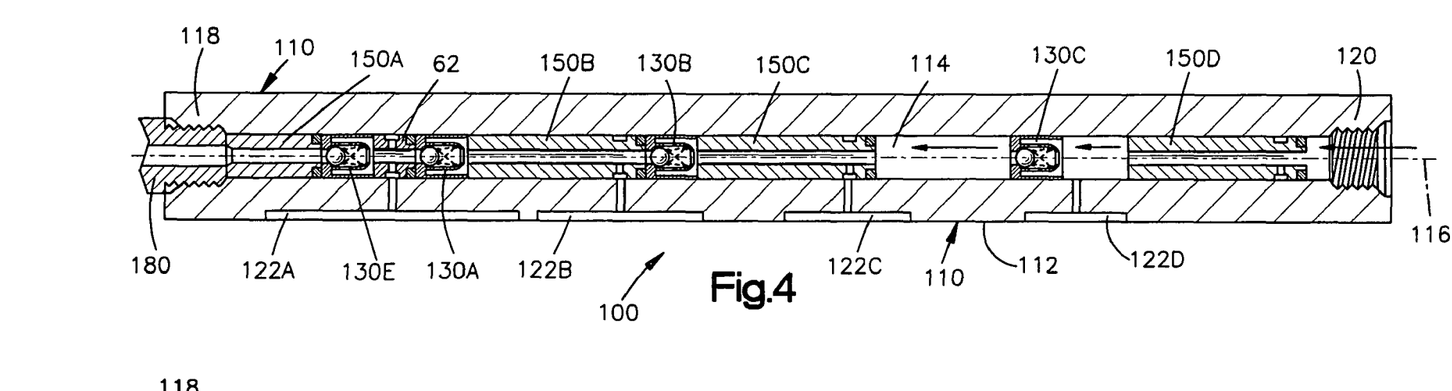
FIG. 4 is an enlarged sectional view of a cylinder head assembly that forms part of the compressor of FIG. 1, shown in a condition being assembled.
Figure 5:
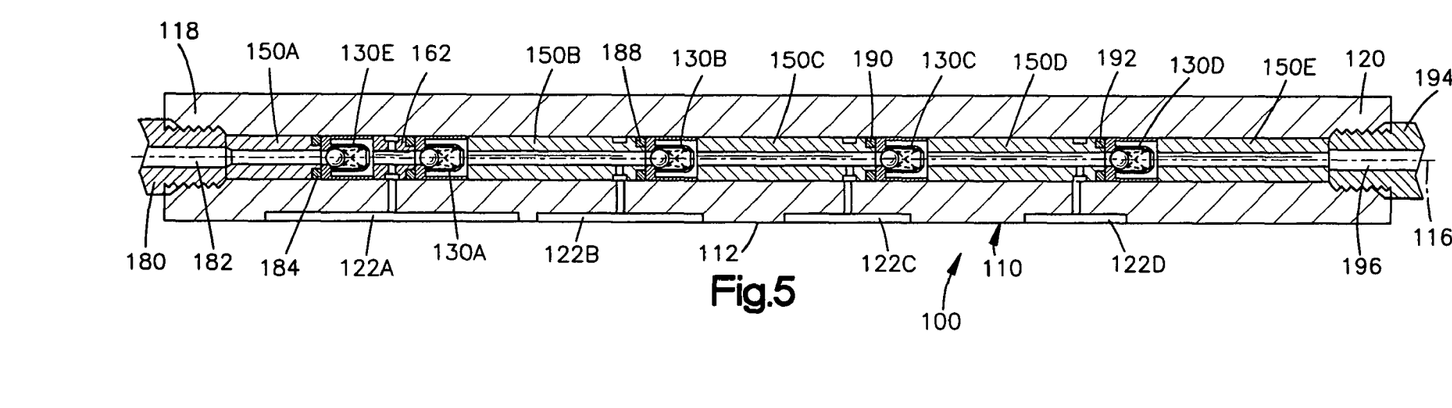
FIG. 5 is a view similar to FIG. 4 showing the cylinder head assembly in an assembled condition.

As shown in FIGS. 4 and 5, the cylinder head 110 is formed as one piece from metal. In the illustrated embodiment, the cylinder head 110 has a rectangular configuration including a planar lower side surface 112. A component chamber 114 extends the length of the cylinder head 110. In the illustrated embodiment, the component chamber 114 has a cylindrical configuration centered on an axis 116. The component chamber 114 has a threaded inlet end portion 118 that forms an inlet of the compressor 10. The component chamber 114 also has a threaded outlet end portion 120 that forms an outlet of the compressor 10.

The cylinder head 110 also has a plurality of charging ports 122A-D that extend between the component chamber 114 and the lower side surface 112. The number of charging ports 122A-D is equal to the number of cylinders 36A-D in the compressor 10. The charging ports 122A-D establish fluid communication between the cylinders 36A-D and the component chamber 114.

A single charging port 122 is associated with each one of the cylinders 36. The charging ports 122A-D extend between the cylinders 36A-D and the upper end surface 32 of the upper cylinder block 30. Thus, the first cylinder 36A has a first charging port 122A, the second cylinder 36B has a second charging port 122B, the third cylinder 36C has a third charging port 122C, and the fourth cylinder 36D has a fourth charging port 122D.

A plurality of components are located in the component chamber 114 of the cylinder head 110. The components direct fluid flow between the inlet 118 of the compressor 10, the cylinders 36A-D and the outlet 120 of the compressor. The components include a plurality of check valves 130A-E for controlling flow of air into and out of the various cylinders 36A-D, and a plurality of spacers for separating and locating the check valves correctly and for directing air to flow between the check valves. The components also include a plurality of seals.

Figure 8:
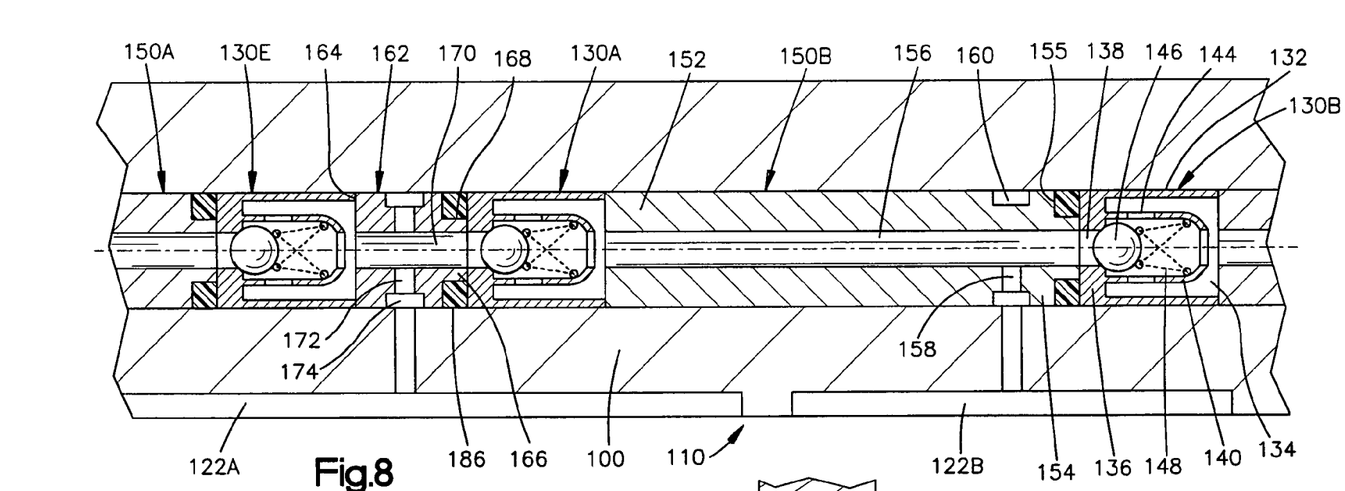
FIG. 8 is a further enlarged view of a portion of the cylinder head assembly of FIG. 5.

As shown in FIG. 8, the several check valves 130A-E that are in the cylinder 110 head are preferably identical to each other. Other types of check valves than that shown can be used. Each check valve 130A-E includes a valve body 132 having a generally cylindrical configuration with a central chamber 134. An end wall 136 is located at the upstream end of the valve body 132. The end wall 136 has a central opening 138. The downstream end of the valve body 132 is open.

The valve body 132 includes a cage 140 that extends axially inward from the end wall 136. The cage 140 has a plurality of ports 144 that establish fluid communication between the interior of the cage 140 and the exterior of the cage.

The check valve 130 includes a movable valve element in the form of a ball 146. The ball 146 is located inside the cage 140 and is movable axially within the cage. The dimensions of the ball 146 are selected so that when the ball is in engagement with the end wall 136 of the valve body 132, the ball closes the opening 138. When the ball 146 is away from the end wall 136, fluid flow is enabled through the cage 140 between the opening 138 and the ports 142 and 144. A spring 148 biases the ball into engagement with the end wall 136.

The components of the cylinder head assembly 100 also include a plurality of long spacers 150A-E that are preferably identical to each other except for their length. Each long spacer 150 is a cylindrical block of metal that has an outside diameter substantially equal to the inside diameter of the component chamber 114 in the cylinder head 10. The long spacer 150 has an upstream end portion 152 and a downstream end portion 154. The downstream end portion 154 has a reduced diameter to form a seal groove 155 at the downstream end of the long spacer 150.

Figure 11:
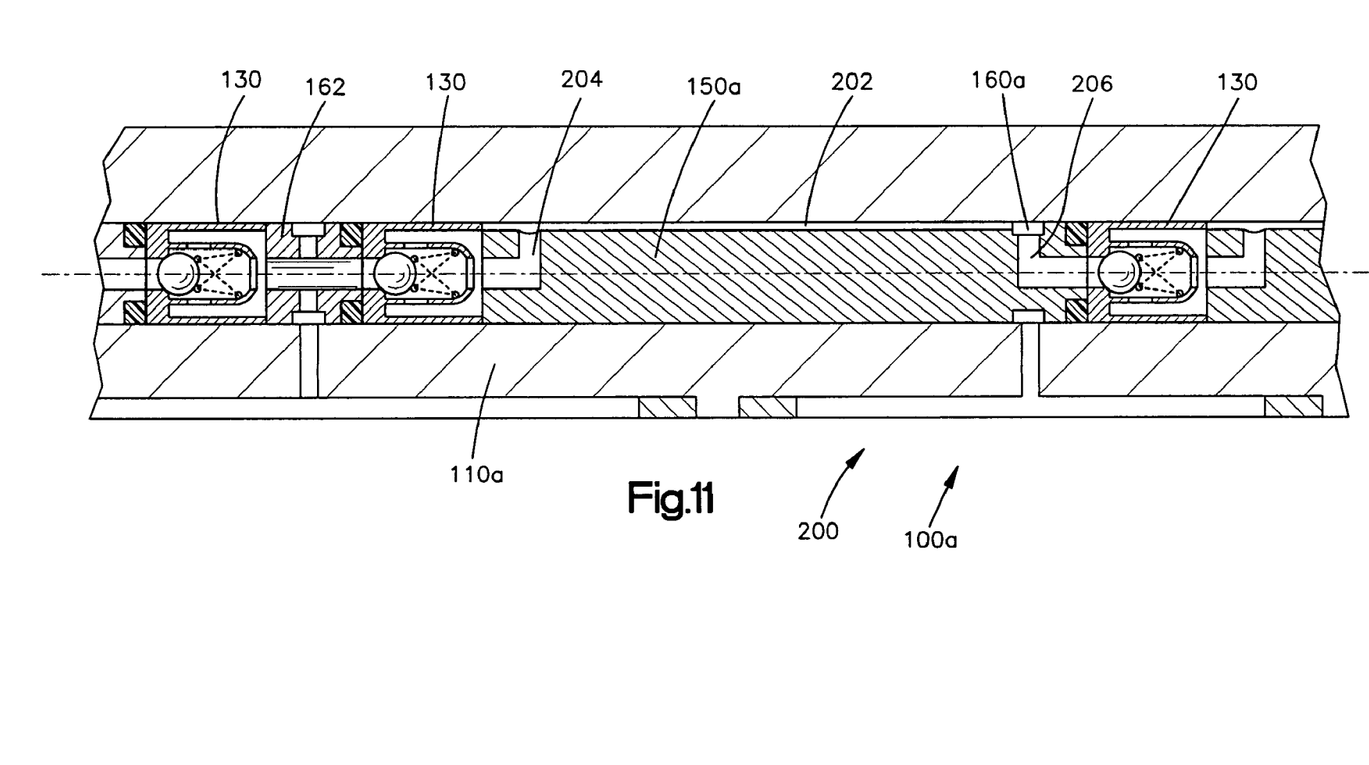
FIG. 11 is an enlarged view of a portion of a cylinder head assembly of the compressor of FIG. 10.

In the particular embodiment of the invention that is illustrated in FIGS. 3-5 and 8, the long spacer 150 has a small diameter central opening 152 that extends for the length of the long spacer between the upstream end portion 152 and the downstream end portion 154. At the downstream end 154 of the spacer, one or more passages 158 extend radially outward from the central opening 156 to an external groove 160. As a result, fluid communication is established between the central opening 156 of the long spacer 150, and the external groove 160. In another embodiment as illustrated in FIG. 11, and as described below, the long spacer has an external groove rather than a central opening, which may be less costly to manufacture.

In one embodiment, the long spacer 150 has an outer diameter of about 5.5 millimeters (about 0.217 inches), and the central passage 156 has a diameter of about 0.030 inches. Because the central opening 156 of the long spacer 150 is small in diameter, the volume of the central opening is small.

The components of the cylinder head assembly 100 include a single short spacer 162. The short spacer 162 is a cylindrical block of metal that has an outside diameter substantially equal to the inside diameter of the component chamber 114 in the cylinder head 110. The short spacer 162 has an upstream end portion 164 and a downstream end portion 166. The downstream end portion 166 has a reduced diameter to form a seal groove 168 at the downstream end of the long spacer.

The short spacer 162 has a small diameter central opening 170 that extends for the length of the short spacer between the upstream end portion 164 and the downstream end portion 166. The short spacer 162 also has a plurality of internal passages 172 that extend radially outward from the central passage 170 and terminate in a groove 174 on the outer surface of the short spacer. As a result, fluid communication is established between the upstream and downstream end portions 164 and 166 of the short spacer 162, and the external groove 174.

As shown in FIG. 3, during assembly of the various components of the cylinder head assembly 110, an inlet connector 180 is screwed into the upstream end of the cylinder head 100. The inlet connector has a fluid inlet passage 182 that communicates with the component chamber.

As shown also in FIG. 5, a seal 184, which may be an O-ring, is placed in the seal groove 155 on the downstream end of a long spacer 150A. The long spacer 150A is inserted or dropped into the component chamber 114 in the cylinder head 110, in a direction from the downstream end of the cylinder head. (The order or direction or manner of assembly can be reversed or changed if desired.) The long spacer 150A engages the inlet connector 180, and the central opening 156 of the long spacer 150A aligns with the fluid inlet passage 182 in the inlet connector.

A first check valve or inlet check valve 130E is inserted or dropped into the component chamber 114 in the cylinder head 110. The upstream end of the inlet check valve 130E engages the downstream end of the long spacer 150A. The opening 138 in the end wall 136 of the inlet check valve 130E aligns with the central passage 156 in the long spacer 150A. The seal 184 seals between the long spacer 150A and the inlet check valve 130F.

A seal 186 (for example an O-ring) is placed in the seal groove 168 on the downstream end of the short spacer 162. The short spacer 162 is inserted or dropped into the component chamber 114 in the cylinder head 110. The upstream end of the short spacer 162 engages the downstream end of the inlet check valve 130E. The external groove 174 on the short spacer 162 aligns with the first charging port 122A in the cylinder head 110. As a result, fluid communication can be established between the component chamber 114 and the first cylinder 36A when the cylinder head assembly 100 is thereafter fastened to the cylinder assembly 12.

A second check valve, or first cylinder check valve, 130A is inserted or dropped into the component chamber 114 in the cylinder head 110. The upstream end of the second check valve 130A engages the downstream end of the short spacer 162. The opening 138 in the end wall 136 of the second check valve 130A aligns with the central passage 170 in the short spacer 162. The seal 186 seals between the short spacer 162 and the second check valve 130A.

Another seal 188 (for example an O-ring) is placed in the seal groove 155 on the downstream end of a second long spacer 150B. The second long spacer 150B is inserted or dropped into the component chamber 114 in the cylinder head 110, in a direction from the downstream end of the cylinder head. The upstream end of the second long spacer 150B engages the downstream end of the first cylinder check valve 130A. The central opening 156 of the second long spacer 150B aligns with the central chamber 134 of the first cylinder check valve 130A.

The external groove 160 at the downstream end of the second spacer 150B aligns with the second charging port 122B in the cylinder head 110. As a result, fluid communication can be established between the component chamber 114 and the second cylinder 36B when the cylinder head assembly 100 is thereafter fastened to the cylinder assembly 14.

A third check valve, or second cylinder check valve, 130B is inserted or dropped into the component chamber 114 in the cylinder head 110. The upstream end of the check valve 130B engages the downstream end of the spacer 150B. The opening 138 in the end wall 136 of the check valve 130B aligns with the central passage 156 in the spacer 150B. The seal 188 seals between the spacer 150B and the check valve 130B.

A seal 190 (for example an O-ring) is placed in the seal groove 155 on the downstream end of a third long spacer 150C. The third long spacer 150C is inserted or dropped into the component chamber 114 in the cylinder head 110, in a direction from the downstream end of the cylinder head. The upstream end of the third long spacer 150C engages the downstream end of the second cylinder check valve 130B. The central opening 156 of the third long spacer 150C aligns with the central chamber 134 of the second cylinder check valve 130B.

The external groove 160 at the downstream end of the third long spacer 150C aligns with the third charging port 122C in the cylinder head 110. As a result, fluid communication can be established between the component chamber 114 and the third cylinder 36C when the cylinder head assembly 100 is thereafter fastened to the cylinder assembly 14.

A fourth check valve, or third cylinder check valve, 130C is inserted or dropped into the component chamber 114 in the cylinder head 110. The upstream end of the fourth check valve 130C engages the downstream end of the long spacer 150C. The opening 138 in the end wall 136 of the fourth check valve 130C aligns with the central passage 156 in the spacer 150C. The seal 190 seals between the spacer and the check valve.

A seal 192 (for example an O-ring) is placed in the seal groove 155 on the downstream end of a fourth long spacer 150D. The fourth long spacer 150D is inserted or dropped into the component chamber 114 in the cylinder head 110, in a direction from the downstream end of the cylinder head. The upstream end of the long spacer 150D engages the downstream end of the third cylinder check valve 130C. The central opening 156 of the spacer 150D aligns with the central chamber 134 of the check valve 130C.

The external groove 160 at the downstream end of the fourth long spacer 150D aligns with the fourth charging port 122D in the cylinder head 110. As a result, fluid communication can be established between the component chamber 114 and the fourth cylinder 36D when the cylinder head assembly 100 is thereafter fastened to the cylinder assembly 14.

A fifth and final check valve or "fourth cylinder check valve" 130D is inserted or dropped into the component chamber 114 in the cylinder head 110. (The terms "fifth check valve" and "fourth check valve" apply here because the illustrated embodiment is a five-cylinder compressor; in a compressor with a different number of cylinders, the numbering of the check valves could be different.) The upstream end of the fourth cylinder check valve 130D engages the downstream end of the spacer 150D. The opening 138 in the end wall 136 of the check valve aligns with the central passage 156 in the spacer 150D. The seal seals 192 between the spacer 150D and the check valve 130D.

An outlet end spacer 150E is inserted or dropped into the component chamber 114 in the cylinder head 110, in a direction from the downstream end of the cylinder head. The upstream end of the outlet end spacer 150E engages the downstream end of the fourth cylinder check valve 130D. A central opening 156 of the spacer 150E aligns with the central chamber 134 of the check valve 130D.

An outlet connector 194 is screwed into the downstream end of the cylinder head 110 to tighten and secure the chain of components in the cylinder head. The outlet connector 194 has a fluid outlet passage 196 that is in fluid communication with the component chamber 114 of the cylinder head 110.

The cylinder head assembly 110, after it is thus assembled, is secured to the other parts of the compressor 10 with the bolts 102, as described above. All the check valves 130A-E of the compressor 10 are located in the cylinder head 110.

All of the check valves of the compressor 10 are disposed in the cylinder head 110 and are supported by the cylinder head for movement with the cylinder head as a unit between a disassembled position spaced apart from the cylinder assembly 12 and an assembled position connected with the cylinder block.

Also, all the charging ports 122A-D and other gas flow passages are located in the cylinder head 110. All fluid flow between the cylinders 36A-36D takes place within the cylinder head assembly 100 and, specifically, within the cylinder head 110.

Referring once again to FIGS. 3 and 5, when the compressor 10 is operating, air is admitted to the compressor through the inlet connector 180. The air flows through the inlet connector 180 and through the first spacer 150A to the inlet check valve 130E.

When the compressor 10 is at the portion of its cycle in which the first cylinder 36A is on the intake phase, the pressure in the first cylinder is lower than the intake pressure. As a result, intake air flows through the inlet check valve 130E and into the short spacer 162, moving the ball 146 off the end wall 136 of the inlet check valve.

The air flows from the central passage 170 of the short spacer 162, radially outward through the passages 172, into the external groove 174 on the short spacer. The air then flows through the first charging port 122A and into the first cylinder 36A.

During this time, the air flowing through the inlet check valve 130E does not flow through the second check valve 130A, even though the short spacer 162 is open for free flow to the second check valve. This is because the pressure downstream of the second check valve 130A, i.e., the pressure in the second cylinder 36B, is higher than the intake pressure. Therefore, the second check valve 130A stays closed and the intake air flows solely into the first cylinder 36A.

When the compressor 10 thereafter has compressed the air in the first cylinder 36A and the first cylinder is on its exhaust phase, the pressure in the first cylinder is higher than the intake pressure. As a result, intake air can not flow upstream through the inlet check valve 130E into the short spacer, in a direction toward the air intake 180. Therefore, all the air flowing out of the first cylinder is directed through the first charging port 122A and the short spacer 162 into the second check valve 130A.

The second check valve 130A opens to allow air to flow out of the first cylinder 36 into the second spacer 150B. The air flows through the second spacer 150B to the radially extending passages 158 and the external groove 160 in the downstream end 154 of the second spacer 150B. The air then flows from the groove 160 into the second charging port 122B.

The timing of the first and second cylinders 36A and 36B is selected so that when the first cylinder 36A is on its exhaust phase, the second cylinder 36B is on its intake phase. Therefore, the air that is compressed in the first cylinder 36A and forced into the second spacer 150B is able to flow into the second cylinder 36B, there to be further compressed because the second cylinder is smaller in diameter than the first cylinder but has the same stroke.

During this time, the air flowing through the second spacer 150 does not flow through the third check valve 130B, even through the second spacer is open to the third check valve. This is because the pressure downstream of the third check valve 130B, i.e., the pressure in the third cylinder 36C, is higher than the pressure at the third check valve. Therefore, the third check valve 130B stays closed and the air that flows through it flows solely into the second cylinder 36B.

In a similar manner, the air that is compressed in the second cylinder 36B flows into the third cylinder 36C, there to be further compressed. The air that is compressed in the third cylinder 36C flows into the fourth cylinder 36D, there to be further compressed. The air that is compressed in the fourth cylinder 36D flows out of the compressor 10 through the outlet connector 194.

During this operation of the compressor 10, each piston-cylinder combination compresses both air that is in "swept volume" of the compressor and air that is in "unswept volume" of the compressor. "Swept volume" is that volume in the respective cylinder 36A-36D that is swept or covered by the moving piston face. "Unswept volume" is volume that is in fluid communication with the piston face when the piston is compressing, but that is not swept or covered by the moving piston face. Even though it is not swept, the air in such a volume is subject to compression by the piston, because it is in fluid communication with the swept volume—there are no valves between to close it off.

In relation to the second cylinder 36B, for example, the unswept volume is in the components of the cylinder head assembly that are located between the first charging port 122A and the second cylinder 36B. This unswept volume is the combination of the internal volume of the second charging port 122B, the internal volume of the first cylinder check valve 130A, and the volume of the second spacer 150B.

When the second cylinder 36B is on its compression phase, the bore of the second cylinder is in fluid communication with this unswept volume. Therefore, the air that is in this unswept volume is also compressed by the second piston 40B. This unswept volume associated with the second cylinder 36B is very small in comparison to the swept volume of the bore of the second cylinder. The central passage 156 in the second long spacer 150B is very small in diameter. Therefore, even though the second spacer 150B is quite long, its internal volume is small. Also, the internal volume of the first cylinder check valve 130A is small. Further, the volume of the second charging port 122B is also small, and large enough to pass the air in and out as needed.

As a result, the total unswept volume between the first cylinder 36A and the second cylinder 36B is relatively small in comparison to the swept volume of the bore of the second cylinder. Therefore, on its intake stroke, the second piston 40B pulls less oxygen from unswept volume, and can pull more oxygen to compress from the previous cylinder.

Similarly, the first third and fourth cylinders 36A, 36C and 36D can compress more effectively, because each is working with a relatively small unswept volume between it and the next upstream cylinder.

Because the unswept volume associated with each one of the cylinders 36A-36D is small, the air being compressed therein can be allowed to flow back upstream, and there is no need for a second check valve for each cylinder to prevent flow of compressed air upstream. Rather, there is needed only one check valve 130 per cylinder 36 (plus the inlet check valve 130E), as opposed to the standard two check valves per cylinder.

Figure 10:
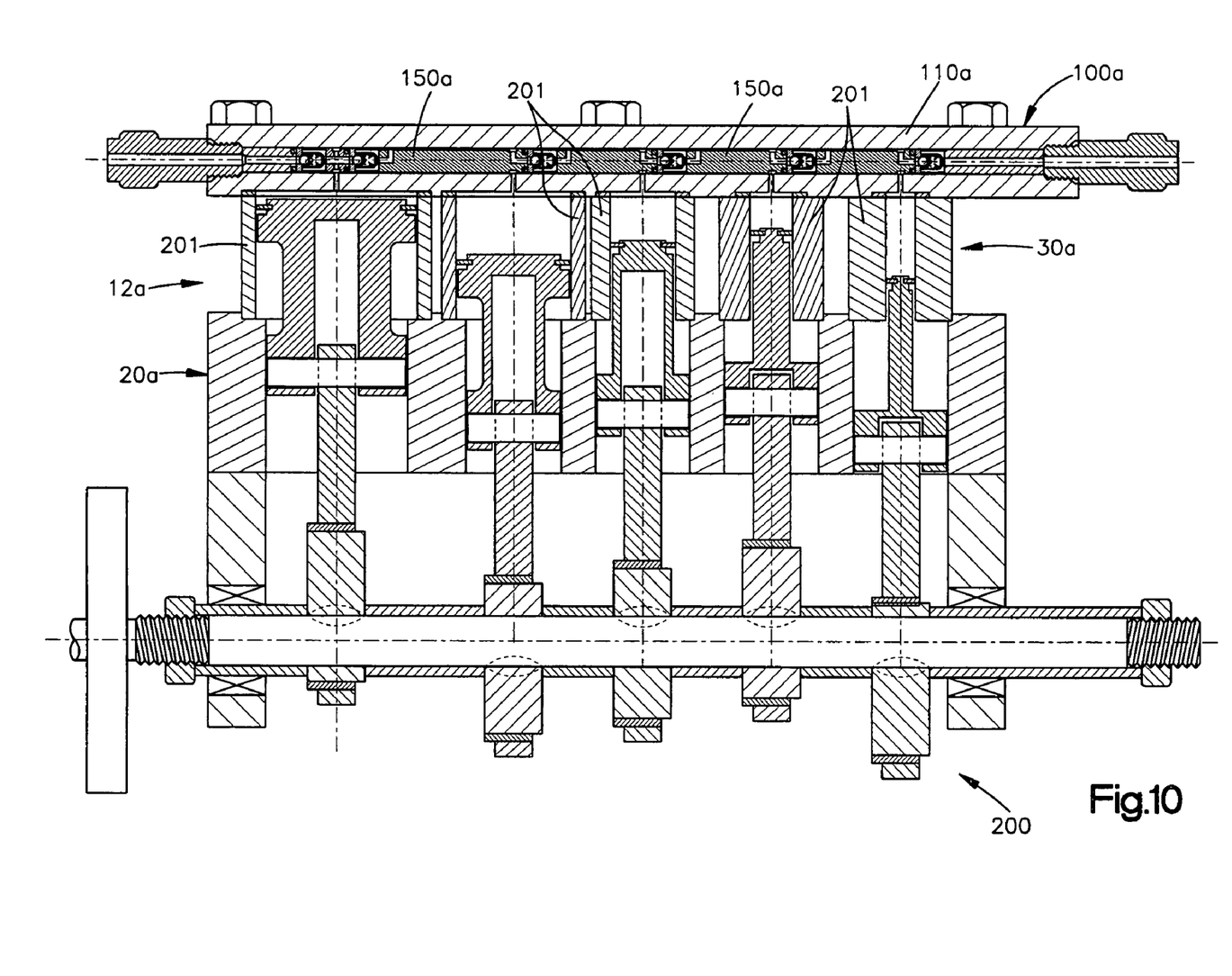
FIG. 10 is a sectional view similar to FIG. 3 of the compressor of FIG. 2.

FIGS. 10 and 11 illustrate a compressor 200 in accordance with a second embodiment of the invention. The compressor 200 has many of the same features as the compressor 10 illustrated in FIGS. 1-9. Parts of the compressor 200 that are the same as or similar in construction or function to corresponding parts of the compressor 10 are given the same reference numerals with the suffix "a" added to distinguish them.

The compressor 200 is a five cylinder model rather than a four cylinder compressor. In addition, the compressor 200 has a different type of cylinder assembly 12a, and some different components in its cylinder head assembly 100a.

Specifically, the compressor 200 has an upper cylinder block 30a that is formed as a plurality of individual cylinder sleeves 201, rather than as a one piece "mono-block" design. The sleeves 201 are set into grooves or recesses in the upper surface of the lower cylinder block 20a.

Also, the compressor 200 uses a different type of long spacer in its cylinder head assembly 100a. Specifically, the long spacers 150a (FIG. 11) do not have a small diameter central passage that extends for the entire length of the piece, which can be difficult and costly to machine. Rather, each one of the long spacers 150a has an exterior groove 202 that extends between L-shaped end passages 204 and 206 on its opposite ends. The downstream passage 206 communicates with an external groove 160a on the downstream end portion of the spacer 150a. Any of these features of either compressor 10 or 200 are usable in conjunction with a four cylinder compressor or a five cylinder compressor (or a compressor having a different number of cylinders).

Figure 12:
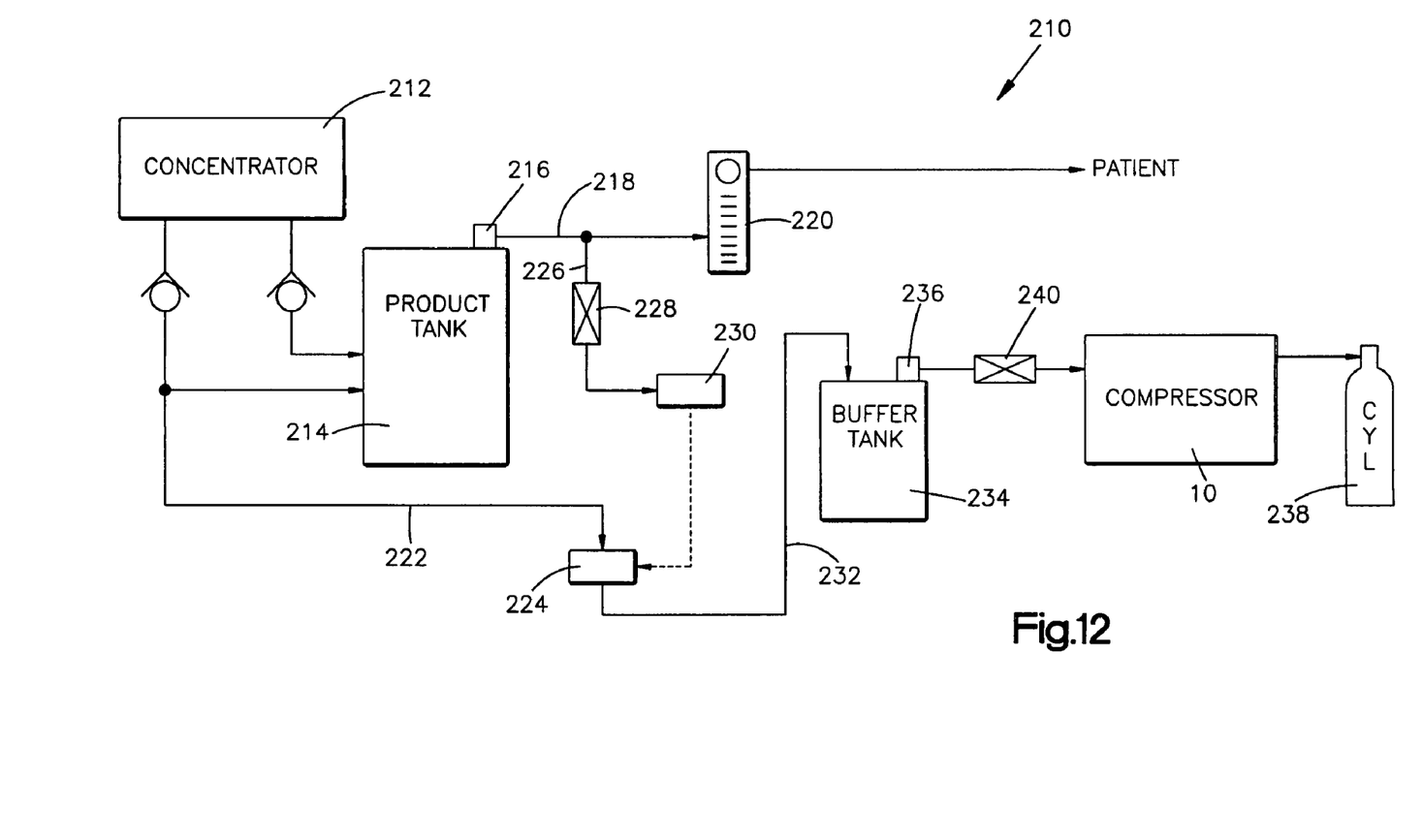
FIG. 12 is a schematic illustration of a first exemplary system of the present invention, including a compressor, for providing oxygen-enriched gas for use by a patient.

Referring to FIG. 12, a system 210 includes a concentrator 212 that is operable to provide oxygen-enriched gas, for example, from an ambient air input. The oxygen-enriched gas is fed to a product tank 214. A 5-psi regulator 216 emits oxygen-enriched gas from the product tank 214 into a flow line 218 and feeds the same to a flow meter 220 which subsequently emits the oxygen-enriched gas to the patient at a predetermined flow rate of from 0.1 to 6 liters per minute. Optionally, the flow meter 220 can be closed so that all the oxygen-enriched gas is directed to the compressor 10.

Gas not directed to the patient is carried via line 222 to two-way valve 224. A very small portion of the gas in the flow line 220 is directed through line 226 and restrictor 228 into an oxygen sensor 230 which detects whether or not the concentration of the oxygen is of a predetermined value, for example, at least 84 percent as directed to the patient and at least 93±3% as directed to the compressor.

When the oxygen sensor 230 detects a concentration at or above the predetermined level, the two-way valve 224 is kept open to permit the oxygen-enriched gas to flow through the valve 224 and line 232 into a buffer tank 234 wherein the pressure is essentially the same as the pressure in the product tank 214. However, should the oxygen sensor 230 not detect a suitable oxygen concentration, two-way valve 224 is closed so that the oxygen concentrator 212 can build up a sufficient oxygen concentration. This arrangement prioritizes the flow of oxygen-enriched gas so that the patient is assured of receiving a gas having a sufficient oxygen concentration therein.

Buffer tank 234 can have a regulator 236 thereon generally set at 12 psi to admit the oxygen-enriched gas to the compressor 10 when needed. The output of the compressor 10 is used to fill a cylinder or portable tank 238 for ambulatory use by the patient. Alternatively, the pressure regulator 236 can be set at anywhere from about 13 to about 21 psi. A restrictor 240 controls the flow rate of gas from the buffer tank 234 to the compressor 10. Should the operation of the compressor 10 cause the pressure in the buffer tank 234 to drop below a predetermined value, a pressure sensor (not shown) automatically cuts off the flow of gas at a pressure above the pressure of the gas being fed to the patient. This prioritization assures that the patient receives priority with regard to oxygen-enriched gas.

Figure 13:
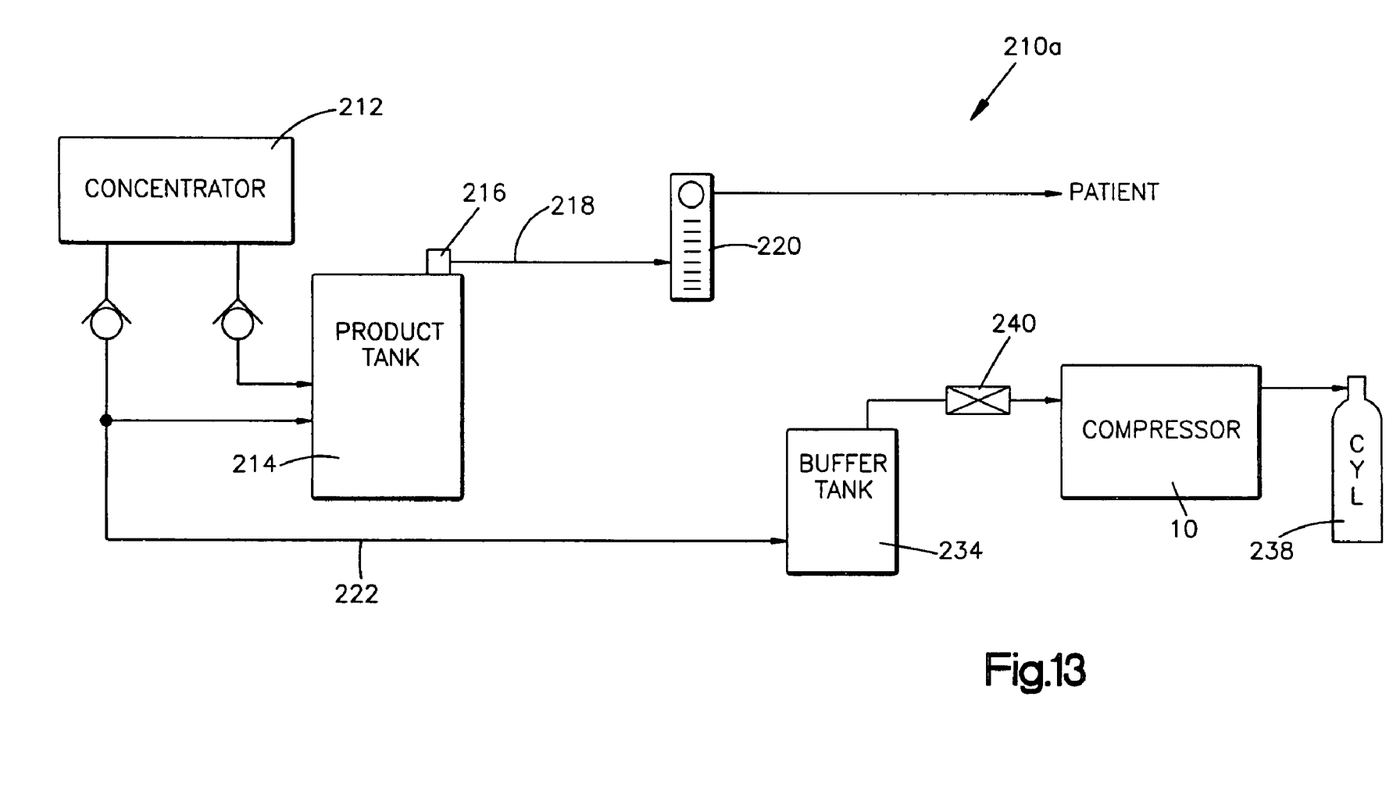
FIG. 13 is a schematic illustration of a second an exemplary system of the present invention, including a compressor, for providing oxygen-enriched gas for use by a patient.

FIG. 13 shows a system 210a that is somewhat different from the system 210 of FIG. 12. In the system 210a, the compressor 10 includes its own oxygen sensor and control circuitry, so that the elements 224-232 are not present as they are in the system shown in FIG. 12. In addition, the regulator 236 is not present on the buffer tank. A flow restrictor may be provided between the concentrator and the buffer tank. (It should be noted that the buffer tank 234 is optional in all systems, and that the compressor could be fed directly from the product tank.)

One five cylinder compressor that is exemplary of the invention has the following dimensions and structural characteristics. The compressor runs at about 90 to 95 rpm. The compressor has a length of about nine to 10 inches, a width (depth) of about three inches, and a height is about 8 inches. In comparison, a prior inline 5 cylinder compressor for this application had a length of about 10 inches, a width (depth) of about 5 inches, and a height of about 18 inches.

The compressor draws two standard liters of oxygen per minute from the concentrator (or other oxygen source). The output of the compressor is in the range of about 2,000 psi.

The cylinder head is 8.4 inches long, 2.125 inches wide, and 0.625 inches tall. The central passage (component chamber 114) in the cylinder head is 0.215 inches in diameter.

The short spacer is 0.189 inches long, with a central passage having a diameter of 0.030 inches. The long spacer is 0.932 inches long, with a generally semi-circular outer side passage having a radius of 0.020 inches.

The exhaust spacer is 0.563 inches long with a central passage of 0.063 inches diameter. The input spacer is 0.653 inches long with a central passage of 0.063 inches diameter.

The unswept volume associated with the first cylinder is 0.00508 cubic inches. The unswept volume associated with the second cylinder is 0.006721 cubic inches. The unswept volume associated with the third cylinder is 0.006063 cubic inches. The unswept volume associated with the fourth cylinder is 0.006063 cubic inches. The unswept volume associated with the fifth cylinder is 0.006063 cubic inches.

The cylinders have the following diameters: first stage, 1.733 inches; second stage, 1.048 inches; third stage, 0.657 inches; fourth stage, 0.413 inches; fifth stage, 0.260 inches. The pistons have a stroke of 0.624 inches.

As a result, swept volume of the first cylinder is about 0.47 cubic inches. This compares with the unswept volume associated with the first cylinder of 0.00508 cubic inches, which is perhaps one percent.

Similarly, the swept volume of the second cylinder is about 0.17 cubic inches. This compares with the unswept volume associated with the first cylinder of 0.006721 cubic inches, which is perhaps four percent.

The foregoing description relates to a four-cylinder compressor and to a five cylinder compressor as exemplary; the invention is applicable to compressors that have different numbers of cylinders. In addition, the invention is applicable to compressors having cylinder heads with different check valve and spacer designs, and the foregoing description relates to two such compressors as exemplary.

Having described the invention, we claim:

1. A compressor for compressing a gas, comprising:
   first and second cylinders;
   first and second pistons received in said first and second cylinders;
   a drive mechanism coupled to the first and second pistons for reciprocating the first and second pistons in the first and second cylinders;
   a cylinder head that includes an inlet portion, an outlet portion, and a component chamber that extends from the inlet portion to the outlet portion, the cylinder head further comprising a first charging port in fluid communication with the component chamber and the first cylinder and a second charging port in fluid communication with the component chamber and the second cylinder;
   a first check valve disposed in the component chamber between the inlet portion and the first charging port;
   a second check valve disposed in the component chamber between the first charging port and the second charging port;
   a third check valve disposed in the component chamber between the second charging port and the outlet end portion;
   wherein each of the first, second and third check valves include a valve body, a spring, and a valve element, wherein the valve body includes a cage that surrounds the spring and the valve element, wherein the valve body includes a central opening and the spring biases the valve element into engagement with the valve body to close the opening;
   a first spacer disposed between the first check valve and the second check valve, wherein the first spacer is a separate component than the cages of the first and second check valves, wherein a first end of the first spacer engages the valve body of the first check valve and a second end of the first spacer engages the valve body of the second check valve, said first spacer being configured to communicate fluid flow from the first check valve to the first charging port and from the first charging port to the second check valve;
   a second spacer disposed between the second check valve and the third check valve, wherein the second spacer is a separate component than the cages of the second and third check valves, wherein a first end of the second spacer engages the valve body of the second check valve and a second end of the second spacer engages the cage of the third check valve, said second spacer being configured to communicate fluid flow from the second check valve to the second charging port and from the second charging port to the third check valve, wherein the second spacer includes an external groove in fluid communication with the second charging port, a central spacer opening in fluid communication with the second check valve and the third check valve, and a radially extending passage that connects the external groove and the central spacer opening.

2. The compressor of claim 1 further comprising first and second guides disposed in first and second guide openings respectively, wherein the first and second guide openings are aligned with the first and second cylinders respectively, wherein the first guide is formed separately from the first piston, and wherein the second guide is formed separately from the second piston.

3. The compressor of claim 2 wherein the first piston is connected to the first guide.

4. The compressor of claim 1 wherein the cage includes a plurality of ports that establish fluid communication between an interior of the cage and an exterior of the cage.

5. The compressor of claim 4 wherein said cage extends axially from an end wall that includes said central spacer opening, wherein said cage is radially outward of said central spacer opening, and wherein said cage is surrounded by a cylindrical outer wall of the valve body.

6. The compressor of claim 5 wherein said valve element is a ball.

7. The compressor of claim 1 wherein the second spacer fills a majority of a volume of the component chamber between the second check valve and the third check valve.

8. The compressor of claim 1 wherein the second spacer fills substantially all of a volume of the component chamber between the second check valve and the third check valve.

9. The compressor of claim 1 wherein the second spacer fills at least ninety percent of a volume of the component chamber between the second check valve and the third check valve.

10. A compressor for compressing a gas, comprising:
    first and second cylinders;
    first and second pistons received in said first and second cylinders;
    a drive mechanism coupled to the first and second pistons for reciprocating the first and second pistons in the first and second cylinders;
    a cylinder head that includes an inlet portion, an outlet portion, and a component chamber that extends from the inlet portion to the outlet portion, the cylinder head further comprising a first charging port in fluid communication with the component chamber and the first cylinder and a second charging port in fluid communication with the component chamber and the second cylinder;
    a first check valve disposed in the component chamber between the inlet portion and the first charging port;
    a second check valve disposed in the component chamber between the first charging port and the second charging port;
    a third check valve disposed in the component chamber between the second charging port and the outlet end portion;
    wherein each of the first, second and third check valves include a valve body, a spring, and a valve element, wherein the valve body includes a cage that surrounds the spring and the valve element, wherein the valve body includes an opening and the spring biases the valve element into engagement with the valve body to close the opening;
    a first spacer disposed between the first check valve and the second check valve, wherein the first spacer is a separate component than the cages of the first and second check valves, wherein a first end of the first spacer abuts the valve body of the first check valve and a second end of the first spacer abuts the valve body of the second check valve, the first spacer includes an external groove in fluid communication with the first charging port, a first spacer central opening in fluid communication with the first check valve and the second check valve, and a radially extending passage that connects the external groove and the first spacer central opening;
    a second spacer disposed between the second check valve and the third check valve, wherein the second spacer is a separate component from the cages of the second and third check valves, wherein a first end of the second spacer abuts the valve body of the second check valve and a second end of the second spacer abuts the valve body of the third check valve, the second spacer includes an external groove in fluid communication with the second charging port, a second spacer central opening in fluid communication with the second check valve and the third check valve, and a radially extending passage that connects the external groove and the central opening.

11. The compressor of claim 10 further comprising first and second guides disposed in first and second guide openings respectively, wherein the first and second guide openings are aligned with the first and second cylinders respectively, wherein the first guide is formed separately from the first piston, and wherein the second guide is formed separately from the second piston.

12. The compressor of claim 11 wherein the first piston is connected to the first guide.

13. The compressor of claim 10 wherein the cage includes a plurality of ports that establish fluid communication between an interior of the cage and an exterior of the cage.

14. The compressor of claim 13 wherein said cage extends axially from an end wall that includes said first and second central spacer openings, wherein said cage is radially outward of said first and second central spacer openings, and wherein said cage is surrounded by a cylindrical outer wall of the valve body.

15. The compressor of claim 14 wherein said valve element is a ball.

16. The compressor of claim 10 wherein the second spacer fills a majority of a volume of the component chamber between the second check valve and the third check valve.

17. The compressor of claim 10 wherein the second spacer fills substantially all of a volume of the component chamber between the second check valve and the third check valve.

18. The compressor of claim 10 wherein the second spacer fills at least ninety percent of a volume of the component chamber between the second check valve and the third check valve.

19. A compressor for compressing a gas, comprising:
first and second cylinders;
first and second pistons received in said first and second cylinders;
a drive mechanism coupled to the first and second pistons for reciprocating the first and second pistons in the first and second cylinders;
a cylinder head that includes an inlet portion, an outlet portion, and a component chamber that extends from the inlet portion to the outlet portion, wherein the component chamber has a constant diameter cylindrical configuration, the cylinder head further comprising a first charging port in fluid communication with the constant diameter cylindrical component chamber and the first cylinder and a second charging port in fluid communication with the constant diameter cylindrical component chamber and the second cylinder;
a first check valve disposed in the component chamber between the inlet and the first charging port;
a second check valve disposed in the component chamber between the first charging port and the second charging port;
a third check valve disposed in the component chamber between the second charging port and the outlet portion;
wherein each of the first, second and third check valves include a valve body, a spring, and a valve element, wherein the valve body has a cylindrical configuration with an outside diameter that is substantially equal to the inside diameter of the constant diameter cylindrical component chamber, wherein the valve body includes a central opening and the spring biases the valve element into engagement with the valve body to close the opening;
a first spacer disposed between the first check valve and the second check valve, wherein the first spacer has a cylindrical configuration with an outside diameter that is substantially equal to the inside diameter of the constant diameter cylindrical component chamber, wherein the first spacer is separate from the valve bodies of the first and second check valves, the first spacer is in fluid communication with the first charging port, the first check valve, and the second check valve;
a second spacer disposed between the second check valve and the third check valve, wherein the second spacer has a cylindrical configuration with an outside diameter that is substantially equal to the inside diameter of the constant diameter cylindrical component chamber, wherein the second spacer is separate from the valve bodies of the second and third check valves, the second spacer is in fluid communication with the second charging port, the second check valve, and the third check valve.

20. The compressor of claim 19 further comprising inlet and outlet connectors in the inlet and outlet portions of the cylinder head to secure the positions of the first second and third check valves and the first and second spacers in the cylinder head.

21. The compressor of claim 19 further comprising inlet and outlet connectors screwed into the inlet and outlet portions of the cylinder head to secure the positions of the first second and third check valves and the first and second spacers in the cylinder head.

22. The compressor of claim 19 wherein a first end of the first spacer abuts the first check valve and a second end of the first spacer abuts the second check valve, wherein a first end of the second spacer abuts the second check valve and a second end of the second spacer abuts the third check valve.

* * * * *